US007276232B2

(12) United States Patent
Kalbe et al.

(10) Patent No.: US 7,276,232 B2
(45) Date of Patent: Oct. 2, 2007

(54) FORMULATION OF MICROORGANISMS FOR USE IN BAIT GELS FOR RODENT CONTROL

(75) Inventors: Jochen Kalbe, Leichlingen (DE); Thomas Böcker, Leichlingen (DE); Stefan Endepols, Köln (DE); Thomas Jäkel, Stuttgart (DE); Sermasakdi Hongnark, Soi Boonsong Sophis (TH)

(73) Assignee: Bayer CropScience AG, Monheim (DE)

( * ) Notice: Subject to any disclaimer, the term of this patent is extended or adjusted under 35 U.S.C. 154(b) by 160 days.

(21) Appl. No.: 10/275,868

(22) PCT Filed: May 4, 2001

(86) PCT No.: PCT/EP01/05077

§ 371 (c)(1),
(2), (4) Date: Jun. 18, 2003

(87) PCT Pub. No.: WO01/84934

PCT Pub. Date: Nov. 15, 2001

(65) Prior Publication Data

US 2004/0037864 A1 Feb. 26, 2004

(30) Foreign Application Priority Data

May 12, 2000 (DE) .......................... 100 23 401

(51) Int. Cl.
*A01N 25/04* (2006.01)
(52) U.S. Cl. .................. 424/84; 424/265.1; 424/270.1; 424/273.1; 424/405; 424/408; 424/409; 424/410; 435/174; 435/177; 435/178; 435/179
(58) Field of Classification Search ................ 435/174, 435/177, 178, 179; 424/84, 265.1, 270.1, 424/271.1, 272.1, 273.1, 405, 409
See application file for complete search history.

(56) References Cited

U.S. PATENT DOCUMENTS 5,925,670 A * 7/1999 Silverman et al. .......... 514/450

2004/0028713 A1 * 2/2004 Hesse et al. ................. 424/405

FOREIGN PATENT DOCUMENTS

| GB | 1371135 | * | 7/1975 |
| WO | 85/00752 | | 2/1985 |
| WO | WO85/00752 | | 2/1985 |
| WO | WO85/00752 | * | 2/1985 |
| WO | 96/25951 | | 8/1996 |

OTHER PUBLICATIONS

Intern. J. Parasitol. 4, (month unavailable) 1974, vol. 4, pp. 447-449, C.M. Rzepczyk, "Evidence of a Rat-Snake Life Cycle for *Sacrocystis*".
Z Parasitenkd. 62, (month unavailable) 1980, pp. 15-30, Helga Brehm und Werner Frank, "Der Entwicklungskreislauf von *Sarcocystis singaporensis* Zaman und Colley, 1976 im End- und Zwishenwirt".
Z. Parasitenkd. 47, (month unavailable) 1975, pp. 169-185, V. Zaman and Frederick C. Colley, Light and Electron Microscopic Observations of the Life Cycle of *Sarcocystis orientalis* sp. n. in the Rat (*Rattus norvegicus*) and the Malaysian Reticulated Python (*Python reticulatus*).
J. Plant Protection. Trop., 2, (month unavailable) 1985, pp. 67-79, B.J. Wood, "Biological Control of Vertebrates-a Review, and an Assessment of Prospects for Malaysia".
Veterinary Parasitology, 45, (month unavailable) 1992, pp. 1-16, P.B. McKenna and W.A.G. Charleston, "The survival of *Sarcocystis gigantea* sporocysts following exposure to various chemical and physical agents".
*T. Jäkel, H. Burgstaller & W. Frank: "*Sarcocystis singaporensis*: Studies on host specificity, pathogenicity and potential use as a biocontrol agent of wild rates.," J. Parasitol., Bd. 82, Nr. 2, 1996, Seiten 280-287, XP001007892 Siehe: Seite 280, recht Sp., Z. 10/11; Seite 281, rechte Sp., Zeile 1-16; Seite 285, rechte Sp., 2. Vollst. Abs.
*T. Jäkel et al.: "Biological control of rodents using *Sarcocystis singaporensis*." Int. J. Parasitol, Bd. 29, 1999, Seiten 1321-1330, XP001007661 Siehe: Seite 1322, rechte Sp., 1. Abs., und 4 ('Discussion').

* cited by examiner

*Primary Examiner*—Neil S. Levy
(74) *Attorney, Agent, or Firm*—Richard E. L. Henderson

(57) ABSTRACT

The present invention relates to compositions containing different stages of pathogenic protozoans in a gel and to their use for controlling rodents.

12 Claims, No Drawings

FORMULATION OF MICROORGANISMS FOR USE IN BAIT GELS FOR RODENT CONTROL

The present patent application has been filed under 35 U.S.C. 371 as a national stage application of PCT/EP01/05077, filed May 4, 2001, which was published in German as International Patent Publication WO 01/84934 on Nov. 15, 2001, and is entitled to the right of priority of German Patent Application 100 23 401.1, filed May 12, 2000.

The present invention relates to compositions containing different stages of pathogenic protozoans in a gel and to their use for controlling rodents.

It is known that protozoa from the group of the Sarcosporidia (phylum Protozoa, class Sporozoa, subclass Coccidia, order Eucoccidiida, suborder Eimeriina) are pathogenic to rodents (Genera *Rattus, Bandicota, Arvicanthis, Nosokia, Mus*) and that a sufficient dose leads to the animals' death (Rzepczyk 1974, Intern. J. Parasitol. 4, 447-449; Brehm, Frank 1980, Z. Parasitenkd. 62, 15-30). A parasite from among this group which is especially pathogenic to several rat species is *Sarcocystis singaporensis* (Zamann et al. 1975, Z. Parasitenkd. 47, 169-185).

The definite hosts of the parasites are predators or omnivores; for *S. singaporensis*, the definite hosts are snakes, for example the reticulated python. The parasite forms sporocysts in the gut of the definite host. These persistent stages are excreted together with the faeces. If an intermediate host, in the case of *S. singaporensis* for example a rat, is infected orally with these sporocysts, sporozoites hatch in the rat's intestines and penetrate the intestinal wall. Via the blood circulation, these stages reach other organs, where they can multiply by division (Schizogony).

Two schizogonies have been detected, the first one around day 6 post-infection and the second around day 14-16 post-infection. The schizonts (merozoites) are found in particularly high numbers in the lungs, where they multiply in the endothelial cells.

If severe infection results in mass multiplication of the merozoites in the lung, the rat falls ill during the second schizogony of the parasite around day 16 post-infection and, in most cases, dies within a few hours.

It is possible to administer the sporocysts of these pathogens to rodents so that the latter die from the infection. This principle can be exploited for controlling rodents (Wood 1985, J. Plant Protect. Trop. 2, 67-69). Rats have already been controlled successfully with *Sarcocystis singaporensis* (Jäkel et al. 1996, J. Parasitol. 82, 280-287).

As a rule, infections of *Rattus rattus* and *norvegicus* with over 20,000 Sporocysts (depending on the strain) are lethal. Up to 14 days post-infection the animals show no symptoms. Then, they weaken rapidly and die of the infection around day 16 post-infection.

Sublethally infected rats show virtually no symptoms of disease, even after 14 days post-infection, and survive the infection without loss of vitality. Only a few days after the infection, these animals have established immunity to the pathogen. These animals are now insensitive to any further control with a *Sarcocystis singaporensis* product.

The sporozoites in aqueous suspension have a shelf life of up to two years without substantial loss of pathogenicity. This suspension can be administered to rats by gavage and, with appropriate dosing, has a lethal effect. However, the sporocysts do not survive in the dry state.

To control rats, baits must be used which are eaten by the animals. Such baits with *S. singaporensis* sporocysts remain pathogenic as long as they are moist. Once dried out, the sporocysts very rapidly lose their pathogenicity. This is why conventional cereal-based baits cannot be used for the effective administration of these parasites. In the applicant's own studies it was impossible to retain the infectivity of *S. singaporensis* sporocysts in cereal-based baits. One day after mixing, these baits had become ineffective.

Baits with sporocysts must be film-packaged in the moist state. The disadvantage of these moist products is the low shelf life since cereal would start to go mouldy, or would germinate, within a few days. One alternative is to dose the liquid suspension in cavities in the bait. For example, lumps of pasty bait whose interior contained a lethal dose of the suspension in a cavity were used successfully. However, these baits too must be used within a few days after preparation since water escapes or since the pasty matrix absorbs water and swells or ferments, rendering these baits useless.

The only possibility as yet for the practical use of protozoa such as *S. singaporensis* for rodent control is to prepare the baits immediately prior to use from a sporocyst-containing aqueous suspension and a bait matrix, for example cereals. The problem here is to withdraw a calculated amount of sporocysts since the latter settle very rapidly in the suspension and concentrate at the bottom of the vessel. This is why baits prepared in this manner contain an indeterminate amount of sporocysts which is not distributed homogeneously. These baits dry rapidly, frequently even during mixing. As a consequence, the sporocysts die and the bait stops being effective after as little as a few hours.

It has now been found, surprisingly, that Sarcocystis sporocysts retain their infectivity for a long time in specific gels, even though it is known from earlier studies that they are no longer infectious on cereals, in pastes and gels such as bentonites after as little as a few days. The fact that they survive over months in the gels described herein was very surprising and unexpected. It is known from the literature that even highly robust sarcosporidia from temperate climates, such as *S. gigantea*, are very sensitive to changes in the pH and chemicals (McKenna et al., Veterinary Parasitology 1992, 45 1-16). It is therefore particularly surprising that even the pH can be varied and in addition preservatives can be added without substantially reducing the parasite's chances of survival.

The present invention therefore makes it possible to preserve sporocysts in gels for the later use in the control of rodents. They remain distributed homogeneously in this matrix. This makes possible the withdrawal of defined quantities of sporocysts. A defined quantity of this gel can be mixed with the bait matrix as long as a homogeneous state has been achieved since the gel is only adsorbed very slowly by the matrix. Since the loss of water, by evaporation, from the gels used is only very slow, the bait remains moist, and thus infectious, even when used in a dry atmosphere.

In this manner, it is possible to store sporocysts over months without suffering gel separation or a considerably reduced infectivity of the pathogens. The appended example, in which a Carbopol gel is used, confirms that such mixtures can be used over several months.

The present invention claims inter alia the principle of preserving stages of single-celled parasites in gels. These gels are used for controlling rodents, either alone or admixed to baits.

Suitable pathogenic organisms are, in principle, all protozoa from the class Sporozoa. Especially suitable are species from the subclass Coccidia. Very specially suitable are representatives of the suborder Eimeriina. Examples which may be mentioned, but not by limitation, are the species of the genus Sarcocystis, such as *S. singaporensis*.

The composition according to the invention can be incorporated into all formulas conventionally used for the production of feed baits for rodents, for example into cereal-based baits, into pastes, gels and wax blocks and into extruded mixtures of cereals and formulation auxiliaries. It is furthermore possible to offer the pathogens in water-based drink baits. The baits for the purposes of the invention are used like conventional baits for controlling harmful rodents. They can be placed in enclosed spaces and in the open, with 5 g to 500 g per bait station, depending on the target species and the bait station density. They can also be placed in the burrow entrances of the rodents to be controlled.

Dosing of the pathogens in the gel can be set as desired. Dosages of from 1000 to 10,000,000 sporocysts/ml are to be preferred. 500,000 to 2,000,000 sporocysts/ml are especially preferred.

The dosage of the pathogens in the bait should amount to 1000 to 200,000 sporocysts per gram of bait. Concentrations of from 2000 to 100,000 sporocysts per gram are preferred, concentrations of 10,000-30,000 are especially preferred and 20,000 sporocysts per gram are particularly preferred. Higher dosages are also possible, but, as a rule, not required. It is possible to employ sporocysts of only one pathogen species or else mixtures of sporocysts of different pathogens.

Harmful and other rodents to be controlled are, for the purposes of the invention, rodents from the order Rodentia. The genera *Rattus, Mus, Bandicota, Nosokia* and *Microtus* are particularly emphasized. The representatives of the genera Rattus and *Bandicota*, e.g. *R. rattus, R. norvegicus, B. benigalensis, B. indica*, are especially to be emphasized.

Gels for the purposes of the invention are water-based and treated with suitable thickeners. Suitable thickeners are macromolecules such as cellulose derivatives, for example hydroxypropylcellulose, hydroxyethylcellulose, methylcellulose, carboxymethylcellulose, hydroxypropylmethylcellulose, hydroxyethylmethylcellulose, hydroxyethylpropylcellulose or xanthans, alginates, polyvinyl alcohols, polyvinylpyrrolidone, polyacrylic acids and their derivatives, or inorganic gellants such as highly-dispersed silica (see, for example, Rudolf Voigt, Pharmazeutische Technologie [Pharmaceutical Technology], pages 362-385, Ulstein Mosby). Particularly suitable are cellulose derivatives and polyacrylic acids.

The water content of the gels can be varied within wide ranges, for example between 30 and 98% by weight, in particular between 50 and 90% by weight and very especially between 70 and 80% by weight.

The pH of the gels can also be varied within wide ranges, for example between pH 2 and 10, in particular between pH 4 and 9, especially preferably between pH 6 and 8.

The gels can be treated with preservatives such as parabens, benzoates, sorbic acid, citrates or parabens, humectants such as glycerol or propylene glycol, antioxidants such as butylhydroxytoluene or butylhydroxyanisole, tocopherol, ascorbic acid, flavourings or other formulation auxiliaries.

In the compositions according to the invention, the sporocysts of the pathogenic protozoa can also be combined with further, including, for example, chemical, active compounds for rodent control. The coumarins may be mentioned here by way of example, but not by limitation.

The compositions according to the invention are prepared by mixing the components in the relevant proportions. Mixing is performed mechanically, for example in stirred vessels or other apparatuses which are suitable for this purpose.

The examples which follow are intended to illustrate the present invention, but without imposing any limitation.

EXAMPLE

Method

The used sporocysts of strain S5 (available at Hohenheim University, Parasitology Department) originate from a Passage in Thailand dated Aug. 17, 1998. A Neubauer haematocytometer was used for counting. The gels were prepared with 1% Carbopol 974 P (Carbopols: weakly crosslinked polyacrylic acids) in water (342 ppm). 2N NaOH was added by titration to adjust the pH. The preservatives used were 0.02% of Solbrol P and 0.14% of Solbrol M (Solbrols: para-hydroxybenzoic acid esters (methyl, ethyl, butyl)). One sample contained 20% of glycerol. 50,000 sporocysts per ml were added to all gels and the gels were mixed thoroughly in order to achieve homogeneous distribution. The gels were kept in the refrigerator at approx. 6° C. and administered at the respective experimental days in accordance with the experimental schedule.

All the experimental animals used were wild *R. norvegicus*. 14 hours prior to being offered the sporocyst bait, the animals were starved and had ad libitum access to water. The bait was based on crushed wheat. Each rat was given 5 g of crushed wheat treated with 1 ml of gel. The rats were again offered standard feed ad libitum only after they had eaten the Sarcocystis bait. Two rats which were observed up to 21 days after dosing were used for each dosage. The parameters determined were the mortality as a function of the gel formulation and the storage period. Rats which showed severe symptoms within the period during which an effect of the pathogen was expected (days 13-17) which would make survival under natural conditions unlikely were destroyed.

Results

TABLE 1

Mortality after the uptake of bait with 50,000 sporocysts (* with 100,000) in various gels on crushed wheat as a function of gel storage time.

| Gel | | | Mortality in (%) after a week's storage time | | | | | | | | | |
|---|---|---|---|---|---|---|---|---|---|---|---|---|
| pH | Solbrol | Glycerol | 0 | 2 | 4 | 6 | 8 | 10 | 12 | 14 | 19 | 24 |
| 6.17 | + | − | 100 | | | 100 | | 100 | | 50 | 0 | |
| 7.04 | + | + | 100 | | | 50 | 0 | | | 0 | 0 | |
| 7.05 | − | − | 100 | 100 | | | 100 | | 0 | | | 50* |
| 8.19 | + | − | 100 | | | 100 | | 100 | | 0 | 0 | |

What is claimed is:

1. A composition comprising sporocysts of pathogenic protozoa in an aqueous gel comprising between 30% and 98% water and a thickener selected from the group consisting of cellulose derivatives, xanthans, polyvinyl alcohols, polyvinylpyrrolidone, polyacrylic acids, and inorganic gellants.

2. A composition according to claim 1 wherein the sporocysts of pathogenic protozoa have a concentration of 1000 to 10,000,000 per ml.

3. A composition for controlling rodents comprising a composition according to claim 1 in addition to one or more rodent bait materials.

4. A method of preparing baits for controlling rodents comprising mixing a composition according to claim 1 with one or more rodent bait materials.

5. A method of controlling rodents comprising placing a composition according to claim 1 in the rodents' environment.

6. A composition according to claim 1 wherein the thickener is selected from the group consisting of polyvinyl alcohols, polyvinylpyrrolidone, polyacrylic acids, and inorganic gellants.

7. A rodent bait comprising sporocysts of pathogenic protozoa in an aqueous gel comprising between 30% and 98% water wherein the sporocysts of pathogenic protozoa have a concentration of 1000 to 200,000 sporocysts per gram of the bait.

8. A rodent bait according to claim 7 wherein sporocysts of pathogenic protozoa have a concentration of 10,000 to 30,000 sporocysts per gram of the bait.

9. A rodent bait according to claim 7 wherein the bait is in the form of a feed bait.

10. A rodent bait according to claim 9 wherein the bait is cereal based.

11. A rodent bait according to claim 7 wherein the bait is in the form of a paste, gel, or wax block.

12. A rodent bait according to claim 7 wherein the bait is in the form of a water-based drink bait.

* * * * *